United States Patent
Gawrys et al.

(10) Patent No.: US 10,285,460 B2
(45) Date of Patent: May 14, 2019

(54) SUPPORT GARMENT

(71) Applicant: INTEGER MEDICAL LLC, Draper, UT (US)

(72) Inventors: Jeffrey Gawrys, Draper, UT (US); Kevin Kay Johanson, Draper, UT (US)

(73) Assignee: Integer Medical LLC, Draper, UT (US)

( * ) Notice: Subject to any disclaimer, the term of this patent is extended or adjusted under 35 U.S.C. 154(b) by 454 days.

(21) Appl. No.: 15/000,405

(22) Filed: Jan. 19, 2016

(65) Prior Publication Data

US 2016/0206021 A1 Jul. 21, 2016

Related U.S. Application Data

(60) Provisional application No. 62/105,349, filed on Jan. 20, 2015.

(51) Int. Cl.
| | |
|---|---|
| *A61F 5/40* | (2006.01) |
| *A41B 9/02* | (2006.01) |
| *A41B 9/12* | (2006.01) |
| *A61F 5/24* | (2006.01) |
| *A41D 13/12* | (2006.01) |
| *A61F 5/30* | (2006.01) |
| *A41D 1/08* | (2018.01) |
| *A61F 5/34* | (2006.01) |
| *A61F 5/32* | (2006.01) |

(52) U.S. Cl.
CPC ............ *A41D 13/1254* (2013.01); *A41B 9/02* (2013.01); *A41B 9/12* (2013.01); *A41D 1/08* (2013.01); *A61F 5/24* (2013.01); *A61F 5/30* (2013.01); *A61F 5/32* (2013.01); *A61F 5/34* (2013.01); *A61F 5/40* (2013.01)

(58) Field of Classification Search
CPC ...... A61F 5/24; A61F 5/30; A61F 5/32; A61F 5/34; A61F 5/40; A41B 9/02; A41B 9/12; A41D 1/08; A41D 13/1254
USPC ....... 602/67, 68, 70–73; 128/98.1, 883, 891; 2/466, 78.1, 109, 400, 401, 403
See application file for complete search history.

(56) References Cited

U.S. PATENT DOCUMENTS

| | | | | |
|---|---|---|---|---|
| 2,055,973 | A * | 9/1936 | Goss | A41B 9/12 128/891 |
| 4,414,971 | A * | 11/1983 | Chung | A61F 5/40 2/405 |
| 4,471,722 | A * | 9/1984 | Dube | A01K 39/02 119/75 |
| 4,526,167 | A * | 7/1985 | Ebenal | A41B 9/023 2/403 |
| 6,622,719 | B1 * | 9/2003 | Slautterback | A61F 5/24 128/98.1 |

(Continued)

*Primary Examiner* — Keri J Nelson
(74) *Attorney, Agent, or Firm* — Kevin K. Johanson (57) ABSTRACT

Techniques for implementing a support garment with at least one support assembly to provide lateral support to a body part, such as the male genitalia. The techniques may be used to provide immobility of the male genitalia following surgical or therapeutic procedures. A support garment for providing support to a male genitalia includes a lower torso portion including an interior surface and an exterior surface. The lower torso portion further includes a groin portion and at least one support assembly extending alongside at least a portion of a male genital region.

18 Claims, 7 Drawing Sheets

(56) References Cited

U.S. PATENT DOCUMENTS

| | | | | |
|---|---|---|---|---|
| 8,398,574 B1* | 3/2013 | Wiens | ............... | A41D 13/0155 128/891 |
| 2014/0026295 A1* | 1/2014 | McIntyre | ............... | A41B 9/02 2/403 |
| 2016/0157531 A1* | 6/2016 | Fisher | .................. | A41D 1/088 2/403 |

* cited by examiner

SUPPORT GARMENT

CLAIM OR PRIORITY UNDER 35 U.S.C. § 119

The present Application for Patent claims priority to Provisional U.S. Application Ser. No. 62/105,349, entitled "SUPPORT GARMENT," filed Jan. 20, 2015, assigned to the assignee hereof, and expressly incorporated herein by reference.

BACKGROUND

Field

The present disclosure relates generally to a therapeutic garment adapted to provide support to a portion of the body.

Background

Various medical procedures require the immobility of portions of the human body. Various medical procedures require the immobility of the male genitalia following surgical or therapeutic procedures. Because of generally elongated nature of the male genitalia, immobility has been uncomfortable and difficult to attain. Techniques for providing support to the male genitalia, for therapeutic or post-surgical recovery would be desirable over existing techniques.

DETAILED DESCRIPTION

The detailed description set forth below is intended as a description of exemplary designs of the present disclosure and is not intended to represent the only designs in which the present disclosure can be practiced. The term "exemplary" is used herein to mean "serving as an example, instance, or illustration." Any design described herein as "exemplary" is not necessarily to be construed as preferred or advantageous over other designs. The detailed description includes specific details for the purpose of providing a thorough understanding of the exemplary designs of the present disclosure. It will be apparent to those skilled in the art that the exemplary designs described herein may be practiced without these specific details. In some instances, well-known structures and devices are shown in block diagram form in order to avoid obscuring the novelty of the exemplary designs presented herein.

Techniques for implementing a support garment with at least one support assembly to provide lateral support to a body part, such as the male genitalia, are described herein. The techniques may be used to provide immobility of the male genitalia following surgical or therapeutic procedures. For clarity, the configuration and use of the techniques for a support garment are described below.

Figure 1:
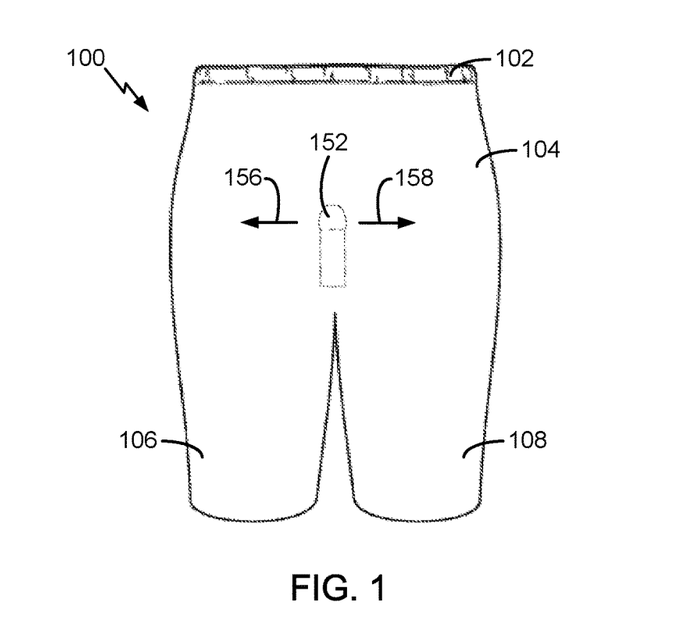
FIG. 1 and FIG. 1A respectively show frontal and cross-sectional views of a garment.
Figure 1A:
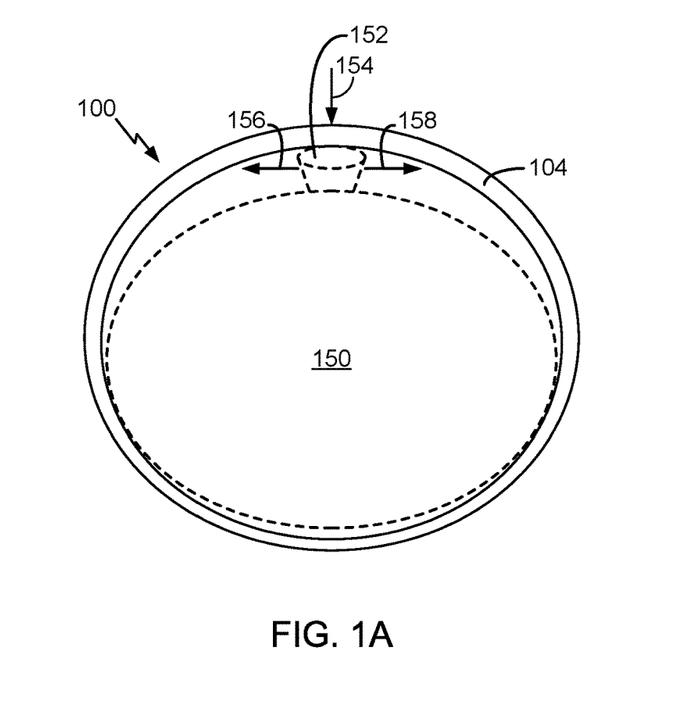

FIG. 1 shows a frontal view of a garment 100. Garment 100 may include a waistband 102 coupled to a lower torso portion 104. Lower torso portion 104 may couple to one or more leg portions 106, 108. Garment 100 may be an undergarment such as underwear or compression shorts. FIG. 1A shows a cross-sectional view of lower torso portion 104 of garment 100 and further shows a cross-sectional view of human torso 150 and male genitalia 152. Garment 100, when donned, may provide compression support 154 to the male genitalia 152, however, garment 100 does not provide lateral support 156, 158 to the male genitalia 152, such as would be advantageous for immobilizing and otherwise protecting from inadvertent jarring or lateral displacement following medical procedures, therapeutic recovery or athletic activity.

Figure 2:
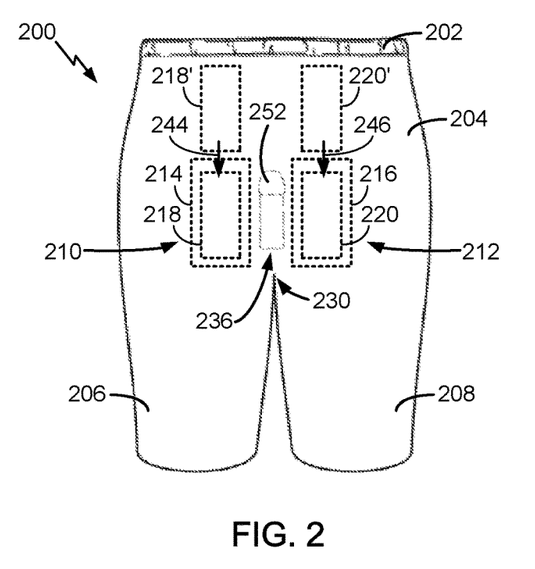
FIG. 2 and FIG. 2A respectively show frontal and cross-sectional views of a support garment, in accordance with one embodiment.

FIG. 2 shows a frontal view of a support garment 200. Support garment 200 may include a waistband 202 coupled to a lower torso portion 204. Lower torso portion 204 may couple to one or more leg portions 206, 208 at crotch region 230. Support garment 200 may be an undergarment such as underwear or compression shorts. Support garment 200 may include one or more support assemblies 210, 212. Support assemblies are coupled to lower torso portion 204 on one or more sides of male genitalia region 236.

Figure 2A:
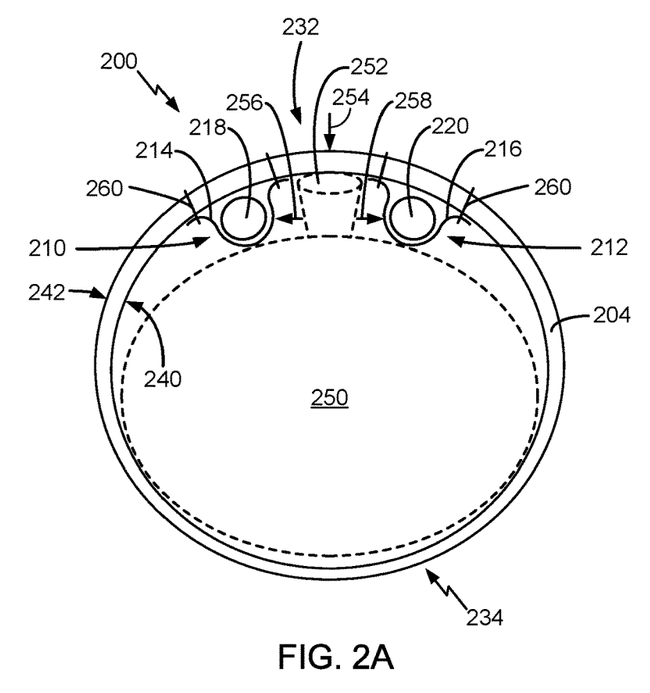

FIG. 2A shows a cross-sectional view of lower torso portion 204 of support garment 200 and further shows a cross-sectional view of human torso 250 and male genitalia 252. Support garment 200, when donned, may provide compression support 254 to the male genitalia 252. Furthermore, support assemblies 210, 212 also provide lateral support 256, 258 to the male genitalia 252. Lower torso portion 204 of support garment 200 further includes an interior surface 240 adjacent to human torso 250 and an exterior surface 242 opposite of the interior surface 240. Lower torso portion 204 further includes a front or groin portion 232 and a back or buttocks portion 234.

Support assemblies 210, 212 in the embodiment of FIG. 2 and FIG. 2A include one or more respective support sleeves 214, 216 affixed or integral to the interior surface 240 of lower torso portion 204 of support garment 200. Support sleeves 214, 216 may be affixed via an attachment 260, such as stitching, fusing, a hook and loop faster (an example of which is commonly sold by VelcroIndustries B.V. under the trademark Velcro®), tape, stapling or other like mechanisms known by those of ordinary skill in the art. In one embodiment, support sleeves 214, 216 may be intrinsically rigid to provide lateral support to the male genitalia 252. In another embodiment, support assemblies 210, 212 may further include one or more support pads 218, 220 within respective support sleeves 214, 216. Furthermore, each support sleeve 214, 216 may receive a plurality or combination of support pads, some of which may provide spacing in the support sleeve for other support pads that may provide support within one or more support sleeves. In one embodiment, support pads 218', 220' may be insertable into respective support sleeves 214, 216 as illustrated by motion arrows 244, 246. In another embodiment, support pads 218, 220 may be integral with (e.g., sewn into or fused with, etc. support sleeves 214, 216 and/or lower torso portion 204 of support garment 200.

Figure 3:
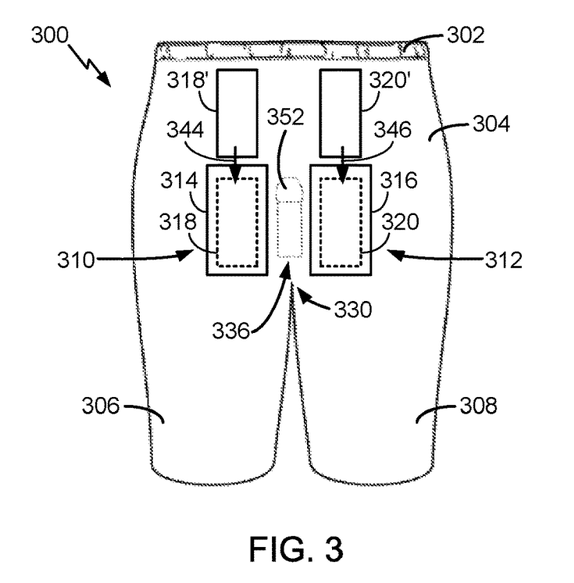
FIG. 3 and FIG. 3A respectively show frontal and cross-sectional views of a support garment, in accordance with another embodiment.

FIG. 3 shows a frontal view of a support garment 300. Support garment 300 may include a waistband 302 coupled to a lower torso portion 304. Lower torso portion 304 may couple to one or more leg portions 306, 308 at crotch region 330. Support garment 300 may be an undergarment such as underwear or compression shorts. Support garment 300 may include one or more support assemblies 310, 312. Support assemblies are coupled to lower torso portion 304 on one or more sides of male genitalia region 336.

Figure 3A:
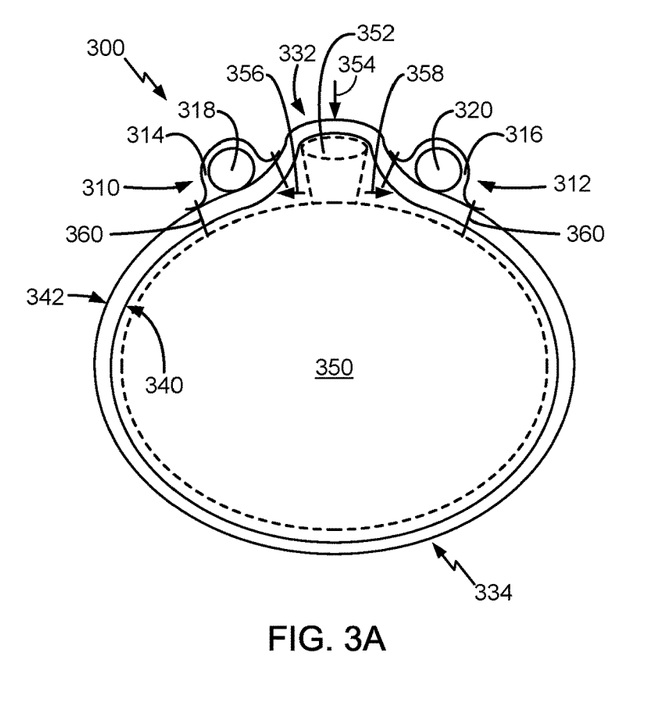

FIG. 3A shows a cross-sectional view of lower torso portion 304 of support garment 300 and further shows a cross-sectional view of human torso 350 and male genitalia 352. Support garment 300, when donned, may provide compression support 354 to the male genitalia 352. Furthermore, support assemblies 310, 312 also provide lateral support 356, 358 to the male genitalia 352. Lower torso portion 304 of support garment 300 further includes an interior surface 340 adjacent to human torso 350 and an exterior surface 342 opposite of the interior surface 340. Lower torso portion 304 further includes a front or groin portion 332 and a back or buttocks portion 334.

Support assemblies 310, 312 in the embodiment of FIG. 3 and FIG. 3A include one or more respective support sleeves 314, 316 affixed or integral to the exterior surface 342 of lower torso portion 304 of support garment 300. Support sleeves 314, 316 may be affixed via an attachment 360, such as stitching, fusing, Velcro®, tape, stapling or other like mechanisms known by those of ordinary skill in the art. In one embodiment, support sleeves 314, 316 may be intrinsically rigid to provide lateral support to the male genitalia 352. In another embodiment, support assemblies 310, 312 may further include one or more support pads 318, 320 within respective support sleeves 314, 316. Furthermore, each support sleeve 314, 316 may receive a plurality or combination of support pads, some of which may provide spacing in the support sleeve for other support pads that may provide support within one or more support sleeves. In one embodiment, support pads 318', 320' may be insertable into respective support sleeves 314, 316 as illustrated by motion arrows 344, 346. In another embodiment, support pads 318, 320 may be integral with (e.g., sewn into or fused with, etc. support sleeves 314, 316 and/or lower torso portion 304 of support garment 300.

Figure 4:
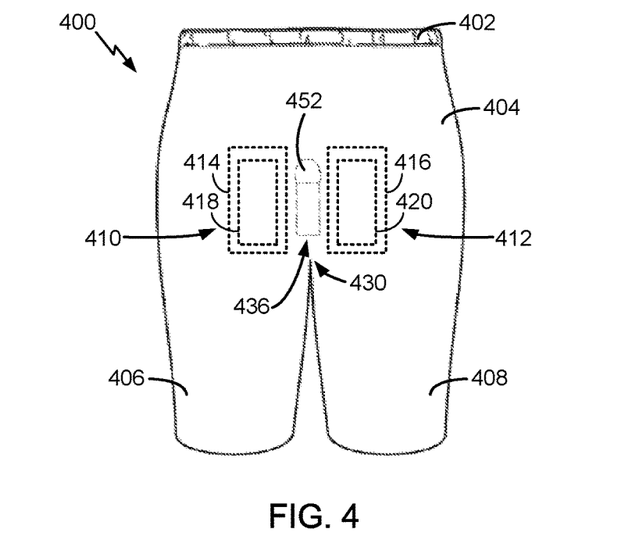
FIG. 4 and FIG. 4A respectively show frontal and cross-sectional views of a support garment, in accordance with yet another embodiment.

FIG. 4 shows a frontal view of a support garment 400. Support garment 400 may include a waistband 402 coupled to a lower torso portion 404. Lower torso portion 404 may couple to one or more lea portions 406, 408 at crotch region 430. Support garment 400 may be an undergarment such as underwear or compression shorts. Support garment 400 may include one or more support assemblies 410, 412. Support assemblies are coupled to lower torso portion 404 on one or more sides of male genitalia region 436.

Figure 4A:
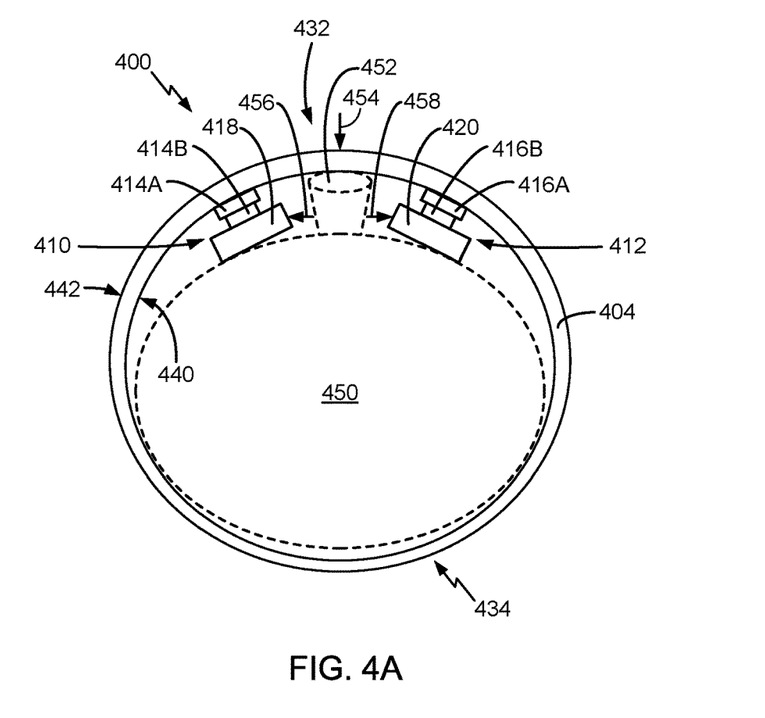

FIG. 4A shows a cross-sectional view of lower torso portion 404 of support garment 400 and further shows a cross-sectional view of human torso 450 and male genitalia 452. Support garment 400, when donned, may provide compression support 454 to the male genitalia 452. Furthermore, support assemblies 410, 412 also provide lateral support 456, 458 to the male genitalia 452. Lower torso portion 404 of support garment 400 further includes an interior surface 440 adjacent to human torso 450 and an exterior surface 442 opposite of the interior surface 440. Lower torso portion 404 further includes a front or groin portion 432 and a back or buttocks portion 434.

Support assemblies 410, 412 in the embodiment of FIG. 4 and FIG. 4A include one or more respective support attachments 414, 416 partially affixed to or integral with the interior surface 440 of lower torso portion 404 of support garment 400. Support attachments 414, 416 may be affixed via stitching, fusing, Velcro®, tape, double-backed tape, stapling or other like mechanisms known by those of ordinary skill in the art. In one embodiment, support attachments 414, 416 each include a two part assembly with one part 414A, 416A attached to the interior surface 440 of lower torso portion 404 and a mating or second part 414A, 416B attached to one or more support pads 418, 420. By way of example and not limitation, support attachments may be Velcro®, snaps, hooks, fusing (e.g., glue) double-backed tape, or any other attachment mechanism known by those of skill in the art. Support assemblies 410, 412 may further include one or more support pads 418, 420 attached via respective support attachments 414, 416. Furthermore, each support attachment 414, 416 may couple a plurality or combination of support pads, some of which may provide spacing for other support pads that may provide support. In one embodiment, support pads 418, 420 may be attachable onto the interior surface of lower torso portion of support garment 400. In another embodiment, support pads 418, 420 may be integral with (e.g., sewn into or fused with) the interior surface 440 of lower torso portion 404 of support garment 400.

Figure 5:
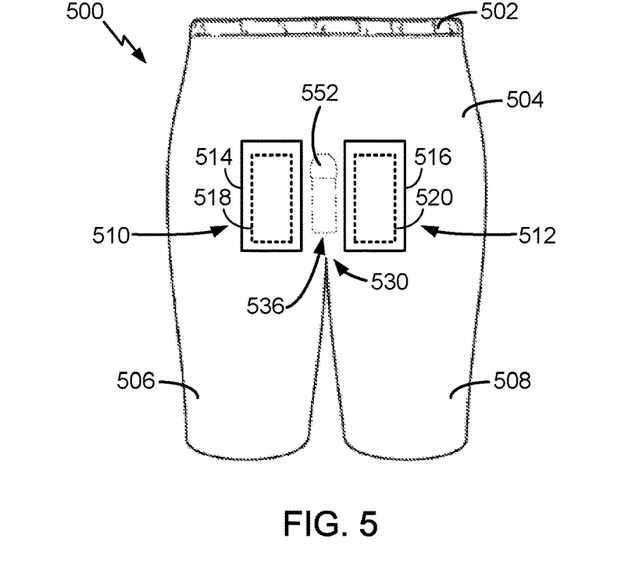
FIG. 5 and FIG. 5A respectively show frontal and cross-sectional views of a support garment, in accordance with yet a further embodiment.

FIG. 5 shows a frontal view of a support garment 500. Support garment 500 may include a waistband 502 coupled to a lower torso portion 504. Lower torso portion 504 may couple to one or more lea portions 506, 508 at crotch region 530. Support garment 500 may be an undergarment such as underwear or compression shorts. Support garment 500 may include one or more support assemblies 510, 512. Support assemblies are coupled to lower torso portion 504 on one or more sides of male genitalia region 536.

Figure 5A:
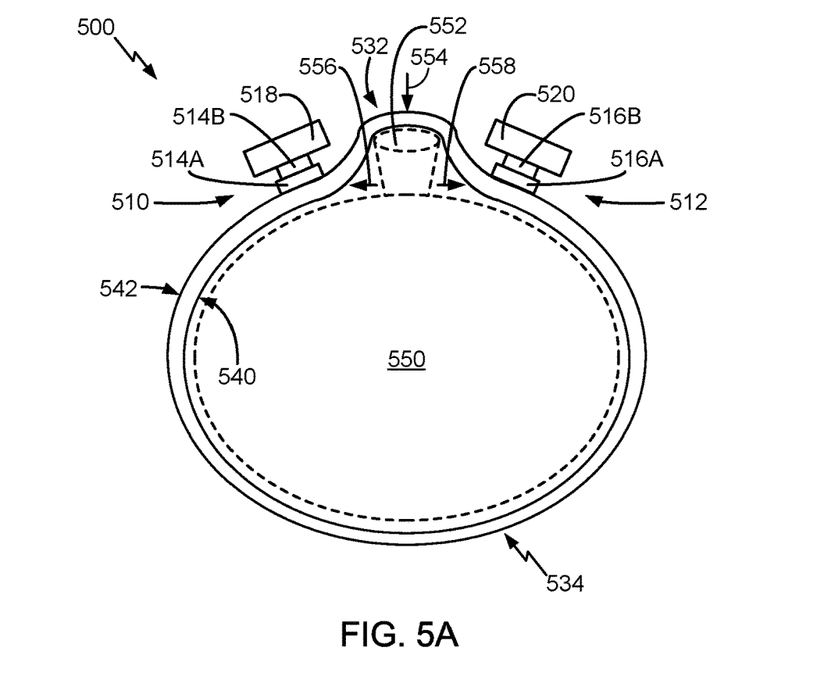

FIG. 5A shows a cross-sectional view of lower torso portion 504 of support garment 500 and further shows a cross-sectional view of human torso 550 and male genitalia 552. Support garment 500, when donned, may provide compression support 554 to the male genitalia 552. Furthermore, support assemblies 510, 512 also provide lateral support 556, 558 to the male genitalia 552. Lower torso portion 504 of support garment 500 further includes an interior surface 540 adjacent to human torso 550 and an exterior surface 542 opposite of the interior surface 540. Lower torso portion 504 further includes a front or groin portion 532 and aback or buttocks portion 534.

Support assemblies 510, 512 in the embodiment of FIG. 5 and FIG. 5A include one or more respective support attachments 514, 516 partially affixed to or integral with the exterior surface 542 of lower torso portion 504 of support garment 500. Support attachments 514, 516 may be affixed via stitching, fusing, Velcro®, tape, double-backed tape, stapling or other like mechanisms known by those of ordinary skill in the art. In one embodiment, support attachments 514, 516 each include a two part assembly with one part 514A, 516A attached to the exterior surface 542 of lower torso portion 504 and a mating or second part 514B, 516B attached to one or more support pads 518, 520. By way of example and not limitation, support attachments may be Velcro®, snaps, hooks, fusing (e.g., glue), double-backed tape, or any other attachment mechanism known by those of skill in the art. Support assemblies 510, 512 may further include one or more support pads 518, 520 attached via respective support attachments 514, 516. Furthermore, each support attachment 514, 516 may couple a plurality or combination of support pads, some of which may provide spacing for other support pads that may provide support. In one embodiment, support pads 518, 520 may be attachable onto the exterior surface of lower torso portion of support garment 500. In another embodiment, support pads 518, 520 may be integral with (e.g., sewn into or fused with) the exterior surface 542 of lower torso portion 504 of support garment 500.

Figure 6:
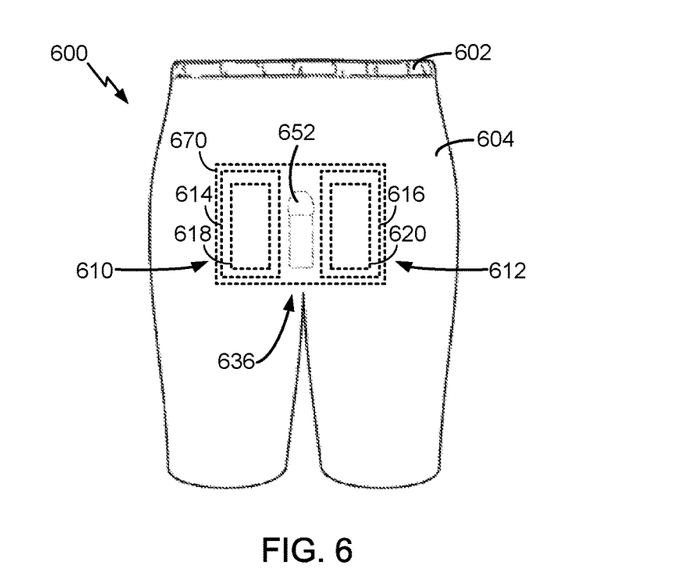
FIG. 6 and FIG. 6A respectively show frontal and cross-sectional views of a support garment, in accordance with another embodiment.

FIG. 6 and FIG. 6B respectively show frontal and cross-sectional views of a support garment, in accordance with another embodiment. FIG. 6 shows a frontal view of a support garment 600. Support garment 600 may be one of support garments 200, 300, 400 and 500. Support garment 600 may include a waistband 602 coupled to a lower torso portion 604. Support garment 600 may be an undergarment such as underwear or compression shorts. Support garment 600 may include one or more support assemblies 610, 612. Support assemblies 610, 612 may be any one of support assemblies 210/212, 310/312, 410/412 and 510/512 of respective FIGS. 3-5A. Support assemblies 610, 612 are coupled to lower torso portion 604 on one or more sides of male genitalia region 636.

Support garment 600 further includes an outer assembly 670 overlaying at least a portion of the male genital region 636. Outer assembly 670 is configured to provide one of padding protection and temperature alteration to the male genital region 636.

Figure 6A:
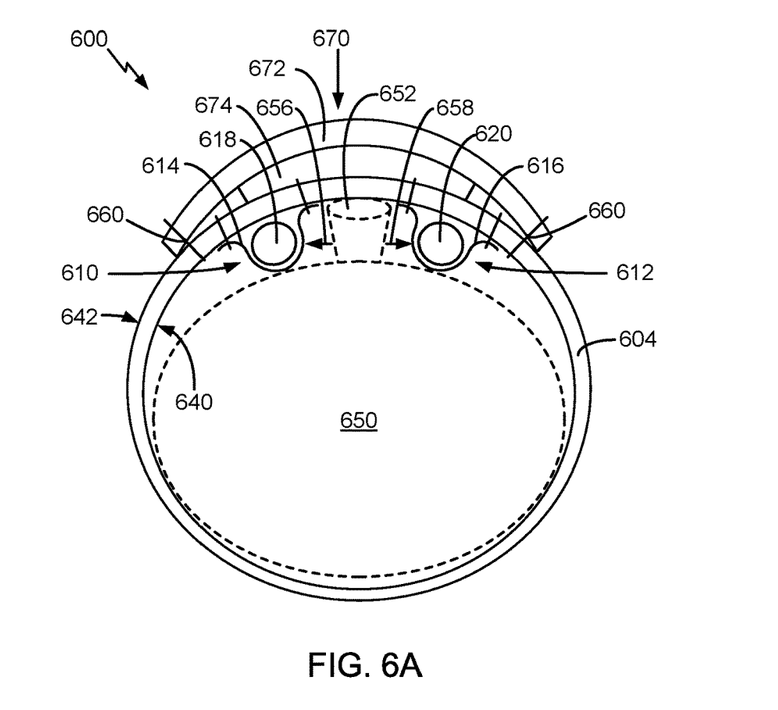

FIG. 6A shows a cross-sectional view of lower torso portion 604 of support garment 600 and further shows a cross-sectional view of human torso 650 and male genitalia 652. Support garment 600, when donned, may provide compression support 654 to the male genitalia 652. Furthermore, support assemblies 610, 612 also provide lateral support 656, 658 to the male genitalia 652. Lower torso portion 604 of support garment 600 further includes an interior surface 640 adjacent to human torso 650 and an exterior surface 642 opposite of the interior surface 640.

Support garment 600 further includes an outer assembly 670 overlaying at least a portion of the male genital region 636. Outer assembly 670 is configured to provide one of padding protection and temperature alteration to the male genital region 636. Outer assembly 670 includes outer sleeve 672 and outer pad 674 (i.e., padding, ice pack, heat pack, etc.). While FIG. 6A illustrates outer assembly 670 affixed to support garment 600 wherein support assemblies 610, 612 are affixed to interior surface 640 of support garment 600, outer assembly 670 may be affixed to support garments 200, 300, 400 and 500. When outer assembly 670 is coupled to one of support garments 200, 300, 400 and 500, the support assemblies are respectively configured as shown in FIGS. 2-5A.

Outer assembly 670 in the embodiment of FIG. 6 and FIG. 6A include one or more outer sleeves 672 affixed or integral to the exterior surface 642 of lower torso portion 604 of support garment 600. Outer sleeve 672 may be affixed via an attachment 660, such as stitching, fusing, Velcro®, tape, stapling or other like mechanisms known by those of ordinary skill in the art. In one embodiment, outer assembly 670 may further include one or more outer pads 674 within respective outer sleeve 672. Furthermore, outer sleeve 672 may receive a plurality or combination of outer pads 674, some of which may provide padding protection and/or temperature alteration of the male genital region 636. In one embodiment, outer pads 674 may be insertable into outer sleeve 672. In another embodiment, outer pad 674 may be integral with (e.g., sewn into or fused with, etc.) outer sleeve 672 and/or lower torso portion 604 of support garment 600.

Support assemblies 610, 612 in the embodiment of FIG. 6 and FIG. 6A include one or more respective support sleeves 614, 616 affixed or integral to the interior surface 640 of lower torso portion 604 of support garment 600. Support sleeves 614, 616 may be affixed via an attachment, such as stitching, fusing, Velcro®, tape, stapling or other like mechanisms known by those of ordinary skill in the art. In one embodiment, support sleeves 614, 616 may be intrinsically rigid to provide lateral support to the male genitalia 652. In another embodiment, support assemblies 610, 612 may further include one or more support pads 618, 620 within respective support sleeves 614, 616. Furthermore, each support sleeve 614, 616 may receive a plurality or combination of support pads, some of which may provide spacing in the support sleeve for other support pads that may provide support within one or more support sleeves. In one embodiment, support pads may be insertable into respective support sleeves 614, 616 and in another embodiment, support pads 618, 620 may be integral with (e.g., sewn into or fused with, etc.) support sleeves 614, 616 and/or lower torso portion 604 of support garment 600.

Figure 7:
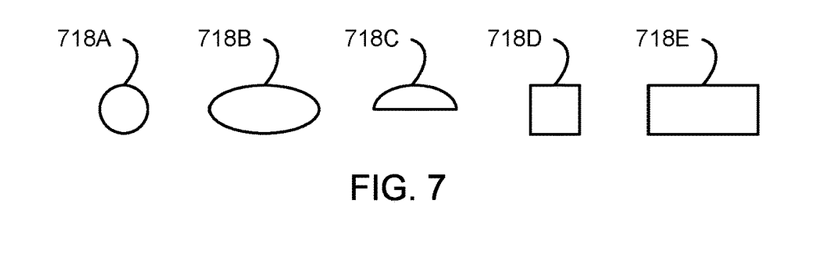
FIG. 7 shows various cross-sectional views of a support pads, in accordance with various embodiments.

FIG. 7 shows various cross-sectional views of a support pads, in accordance with various embodiments. Support pads 218/220, 318/320, 418/420 and 518/520 may be configured to have various shapes and sizes. By way of example, support pads may include various cross-sectional configurations including cross-sections 718A-718E. Other dimensions for support pads known by those of ordinary skill in the art are also contemplated.

Figure 8:
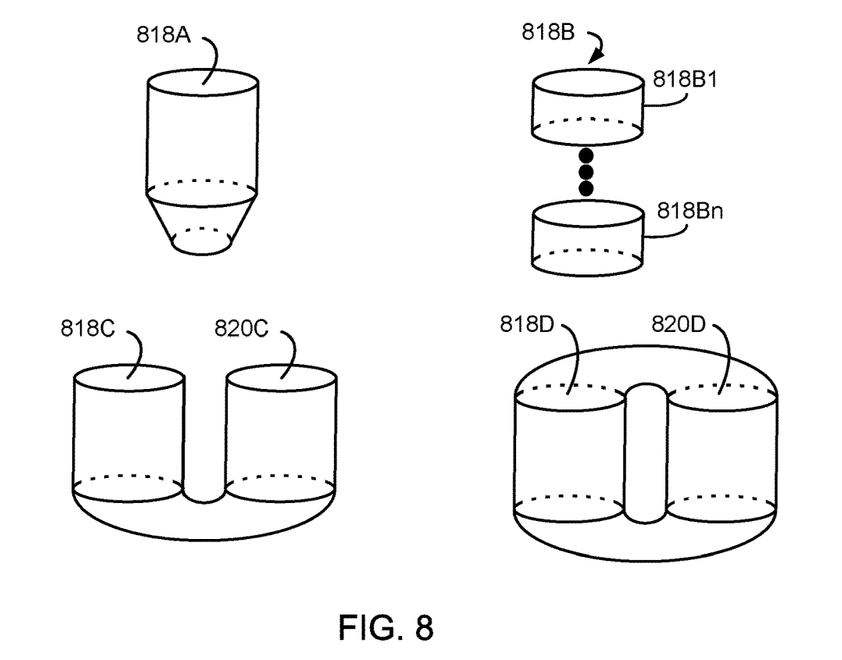
FIG. 8 shows various views of contours and arrangements of support pads, in accordance with various embodiments.

FIG. 8 shows various views of contours and arrangements of support pads, in accordance with various embodiments. Support pads 218/220, 318/320, 418/420 and 518/520 may be configured to have various shapes and sizes. By way of example, support pads may include various configurations. Support pads may include tapered support pads 818A, segmented support pads 818B. U-shaped support pads 818C, 820C and oval/rectangular shaped support pads 818D, 820D. Other shapes and dimensions for support pads know by those of ordinary skill in the all are also contemplated.

Figure 9:
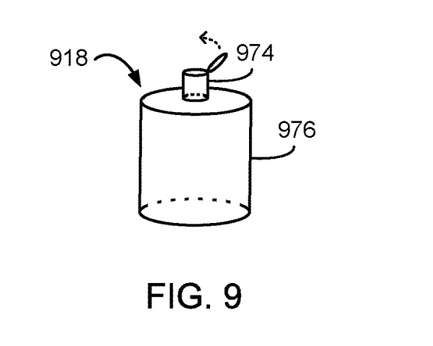
FIG. 9 shows a view of a fillable support pad, in accordance with an embodiment.

FIG. 9 shows a view of a fillable support pad, in accordance with an embodiment. Support pads comprised of various supportable material are contemplated. Further, support pads such as support pad 918 may be configured to receive a liquid or gas through a valve 974 to be confined within vessel 976. Support pad 918 may be inserted into the various support sleeves describe above and then be filled with one or more gases or liquids. It is further contemplated that support pad 918 may include an exit valve (not shown) which could facilitate recirculation of gases or liquids.

The previous description of the disclosure is provided to enable any person skilled in the art to make or use the disclosure. Various modifications to the disclosure will be readily apparent to those skilled in the art, and the generic principles defined herein may be applied to other variations without departing from the scope of the disclosure. Thus, the disclosure is not intended to be limited to the examples and designs described herein but is to be accorded the widest scope consistent with the principles and novel features disclosed herein.

What is claimed is:

1. A support garment, comprising:
   a lower torso portion including an interior surface and an exterior surface, the lower torso portion further including a groin portion;
   a waistband coupled to a top of the lower torso portion; and
   a first support assembly and a second support assembly independent of the first support assembly, the first and second support assemblies configured to respectively extend alongside a first side and an opposite second side and substantially parallel with at least a portion of a male genitalia while the male genitalia extends toward the waistband, the first and second support assemblies further configured to independently support the male genitalia to extend toward the waistband, and yet further configured to independently reduce respective lateral displacement of the male genitalia while the male genitalia rests against a torso and while the male genitalia extends toward the waistband.

2. The support garment of claim 1, wherein the first support assembly and the second support assembly comprises a support sleeve coupled to the lower torso portion and a support pad within the support sleeve.

3. The support garment of claim 2, wherein the support sleeve is configured to have the support pad inserted therein.

4. The support garment of claim 2, wherein the support pad is enclosed with the support sleeve.

5. The support garment of claim 1, wherein at least one of the first support assembly and the second support assembly comprises an attachable support pad coupled to the lower torso portion.

6. The support garment of claim 5, wherein the attachable support pad is removeably attachable to the lower torso portion.

7. The support garment of claim 5, wherein the attachable support pad is fixedly attachable to the lower torso portion.

8. The support garment of claim 1, wherein at least one of the first support assembly and the second support assembly is coupled to the interior surface of the lower torso portion.

9. The support garment of claim 1, wherein at least one of the first support assembly and the second support assembly is coupled to the exterior surface of the lower torso portion.

10. The support garment of claim 1, wherein at least one of the first support assembly and the second support assembly is configured to be filled with one of air and liquid.

11. The support garment of claim 1, further comprising an outer assembly configured to overlay at least a portion of the male genital, the outer assembly configured to provide one of padding protection and temperature alteration to the male genital.

12. The support garment of claim 11, the outer assembly including an outer sleeve coupled to the lower torso portion and an outer pad with the outer sleeve.

13. The support garment of claim 12, the outer pad including one of padding, an ice pack and a heat pack.

14. The support garment of claim 1, wherein at least one of the first support assembly and the second support assembly comprises at least one support pad.

15. The support garment of claim 14, wherein the at least one support pad includes a cross-section that is substantially one of an oval or rectangle.

16. The support garment of claim 14, wherein the at least one support pad is configured to have a shape that is one of substantially cylindrical, U-shaped or oval-shaped.

17. A method, comprising:
    supporting a male genitalia from lateral displacement using a first support assembly and a second support assembly independent of the first support assembly, the first and second support assemblies configured to respectively extend alongside a first side and an opposite second side and substantially parallel with at least a portion of a male genitalia while the male genitalia extends toward a waistband in a lower torso portion of a support garment, the first and second support assemblies further configured to independently support the male genitalia to extend toward the waistband, and yet further configured to independently reduce respective lateral displacement of the male genitalia while the male genitalia rests against a torso and while the male genitalia extends toward the waistband.

18. A support garment, comprising:
    a means for supporting a male genitalia from lateral displacement including a first support assembly and a second support assembly independent of the first support assembly, the first and second support assemblies configured to respectively extend alongside a first side and an opposite second side and substantially parallel with at least a portion of a male genitalia while the male genitalia extends toward a waistband in a lower torso portion of the support garment, the first and second support assemblies further configured to independently support the male genitalia to extend toward the waistband, and yet further configured to independently reduce respective lateral displacement of the male genitalia while the male genitalia rests against a torso and while the male genitalia extends toward the waistband.

* * * * *